(12) United States Patent
Huang et al.

(10) Patent No.: US 10,946,062 B2
(45) Date of Patent: Mar. 16, 2021

(54) USE OF RECOMBINANT PROTEIN FOR TREATING METABOLIC DISORDERS

(71) Applicant: Eusol Biotech Co., Ltd., Taipei (TW)

(72) Inventors: Jin-Ding Huang, Taipei (TW); Wan-Ya Chang, Taipei (TW); Che-Ming Yeh, Taipei (TW)

(73) Assignee: EUSOL BIOTECH CO., LTD., Taipei (TW)

( * ) Notice: Subject to any disclaimer, the term of this patent is extended or adjusted under 35 U.S.C. 154(b) by 0 days.

(21) Appl. No.: 16/802,171

(22) Filed: Feb. 26, 2020

(65) Prior Publication Data

US 2020/0276264 A1 Sep. 3, 2020

Related U.S. Application Data

(60) Provisional application No. 62/811,616, filed on Feb. 28, 2019.

(51) Int. Cl.
*A61K 38/16* (2006.01)
*A61P 3/08* (2006.01)
*A61K 9/00* (2006.01)

(52) U.S. Cl.
CPC .............. *A61K 38/16* (2013.01); *A61P 3/08* (2018.01); *A61K 9/0019* (2013.01)

(58) Field of Classification Search
CPC .......... A61K 38/16; A61K 9/0019; A61P 3/08
USPC ........................................ 514/1.1, 6.9, 21.2
See application file for complete search history.

(56) References Cited

U.S. PATENT DOCUMENTS 7,956,033 B2 * 6/2011 Cheng .................. C07K 14/501
514/9.1

FOREIGN PATENT DOCUMENTS

| CN | 105793281 A | 7/2016 |
| TW | I363761 B | 5/2012 |

OTHER PUBLICATIONS

Metabolic disorder from Merck Manual, pp. 1-4. Accessed Sep. 17, 2020. (Year: 2020).*
Diabetes Mellitus from Merck Manual, pp. 1-13. Accessed Sep. 17, 2020. (Year: 2020).*
English translation of the Written Opinion of the International Searching Authority for International Application No. PCT/CN2020/076730, dated Apr. 24, 2020.
Suh et al., "Endocrinization of FGF1 produces a neomorphic and potent insulin sensitizer," Nature, vol. 513, No. 7518, Sep. 18, 2014, pp. 436-439, 21 pages total.
Wang et al., "FGF1: a Potential Drug for Diabetes Mellitus," Chinese Journal of Biochemistry and Molecular Biology, vol. 34, No. 10, 2018, pp. 1037-1044, 6 pages total, with an English abstract.

* cited by examiner

*Primary Examiner* — Julie Ha
(74) *Attorney, Agent, or Firm* — Birch, Stewart, Kolasch & Birch, LLP

(57) ABSTRACT

Disclosed are methods and compositions useful in preventing or treating a metabolic disorder by using a protein having an amino acid sequence as set forth in SEQ ID NO: 1.

5 Claims, 1 Drawing Sheet

Specification includes a Sequence Listing.

*P<0.05, P<0.01 and *P<0.001, treated vs. vehicle control by two-way ANOVA followed by Bonferroni test.

*P<0.05, P<0.01 and *P<0.001, treated vs. vehicle control by two-way ANOVA followed by Bonferroni test.

USE OF RECOMBINANT PROTEIN FOR TREATING METABOLIC DISORDERS

CROSS REFERENCE TO RELATED APPLICATION

This non-provisional application claims the benefit under 35 U.S.C. § 119(e) to U.S. Provisional Application No. 62/811,616, filed on Feb. 28, 2019, which is hereby expressly incorporated by reference into the present application.

BACKGROUND OF THE INVENTION

Metabolic disorders such as type 2 diabetes mellitus (T2DM) and other related complications are leading causes of mortality. These disorders are associated with the excessive nutritional intake and lack of exercise of the Western lifestyle, which is increasing all over the world. T2DM (and insulin resistant conditions) is a chronic, progressive, incompletely understood metabolic condition mainly characterized by hyperglycemia (a state of long-term elevated levels of glucose in the blood). Impaired insulin secretion, resistance to tissue actions of insulin, or a combination of both are thought to be the commonest reasons contributing to the pathophysiology of T2DM, a spectrum of disease originally arising from tissue insulin resistance and gradually progressing to a state characterized by complete loss of secretory activity of the beta cells of the pancreas. Prolonged high blood sugar may cause blood vessel and nerve damage. The incidence of type 2 diabetes is high and rising and is becoming a leading cause of mortality, morbidity, and healthcare expenditure throughout the world.

Various pharmacological approaches for the treatment of T2DM are available. The major classes of oral antidiabetic medications include biguanides, sulfonylureas, meglitinide, thiazolidinedione (TZD), dipeptidyl peptidase 4 (DPP-4) inhibitors, sodium-glucose cotransporter (SGLT2) inhibitors, and α-glucosidase inhibitors. However, the above approaches have some side effects such as hypoglycemia and weight gain.

Accordingly, there is still a need for improved therapeutic approaches to metabolic disorders with fewer side effects.

SUMMARY OF THE INVENTION

It was unexpectedly found in the present invention that a recombinant protein having an amino acid sequence as set forth in SEQ ID NO: 1 (called "ES135" hereinafter) is effective in treating metabolic disorders. For instance, when administering ES135 to a subject suffering from a metabolic disorder, hyperglycemia, the level of blood glucose was significantly attenuated.

Accordingly, one aspect of the present invention is directed to compositions for preventing or treating metabolic disorders, wherein the compositions comprise ES135. Also provided herein are methods for preventing or treating metabolic disorders comprising administrating an effective amount of ES135.

It is to be understood that both the foregoing general description and the following detailed description are exemplary and explanatory only and are not restrictive of the invention.

DETAILED DESCRIPTION OF THE INVENTION

I. Introduction

Figure 1:
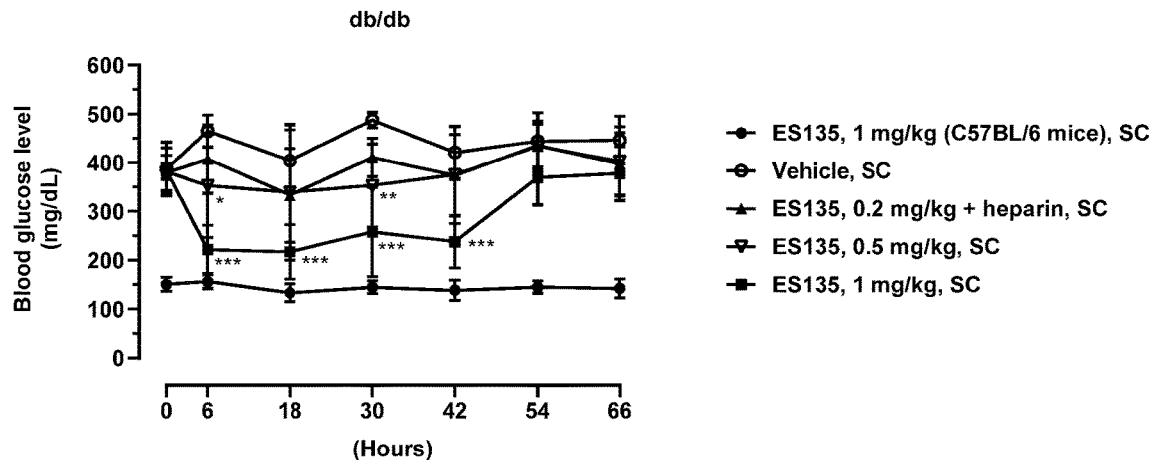
FIG. 1 shows the glucose-lowering effect of different dosages of ES135 in C57BL/6 and db/db mice.

Provided herein are methods and compositions useful in preventing or treating metabolic disorders by using ES135. Based on the studies in diabetic mouse model as described herein, the inventors have shown that ES135 is effective in attenuating the level of blood glucose as compared to the vehicle group.

II. Definitions

The following abbreviations are used herein:
IM (i.m.): intramuscular injection
IV (i.v.): intravenous injection
IP (i.p.): intraperitoneal injection
SC (s.c.): subcutaneous injection
PO (p.o.): oral administration
ICV (i.c.v.): intracerebroventricular injection
IT: intrathecal injection
Bid: bis in die (twice daily)

Unless defined otherwise, technical and scientific terms used herein have the same meaning as commonly understood by a person of ordinary skill in the art. Any methods, devices and materials similar or equivalent to those described herein can be used in the practice of this invention. The following definitions are provided to facilitate understanding of certain terms used frequently herein and are not meant to limit the scope of the present disclosure.

As used herein, the article "a" or "an" means one or more than one (that is, at least one) of the grammatical object of the article, unless otherwise made clear in the specific use of the article in only a singular sense.

As used herein, the term "ES135" refers to a recombinant protein comprising an amino acid sequence of SEQ ID NO: 1, which was disclosed in U.S. Pat. No. 7,956,033, the content of which is hereby incorporated by reference herein in its entirety. The amino acid sequence of SEQ ID NO:1 is as follows: Ala Asn Tyr Lys Lys Pro Lys Leu Leu Tyr Cys Ser Asn Gly Gly His Phe Leu Arg Ile Leu Pro Asp Gly Thr Val Asp Gly Thr Arg Asp Arg Ser Asp Gln His Ile Gln Leu Gln Leu Ser Ala Glu Ser Val Gly Glu Val Tyr Ile Lys Ser Thr Glu Thr Gly Gln Tyr Leu Ala Met Asp Thr Asp Gly Leu Leu Tyr Gly Ser Gln Thr Pro Asn Glu Glu Cys Leu Phe Leu Glu Arg Leu Glu Glu Asn His Tyr Asn Thr Tyr Ile Ser Lys Lys His Ala Glu Lys Asn Trp Phe Val Gly Leu Lys Lys Asn Gly Ser Cys Lys Arg Gly Pro Arg Thr His Tyr Gly Gln Lys Ala Ile Leu Phe Leu Pro Leu Pro Val Ser Ser Asp. In some embodiments, the sequence of ES135 is at least 70%, 75%, 80%, 85%, 90%, 95%, 98%, or 100% identical to the amino acid sequence of SEQ ID NO: 1. In some embodiments, the amino acid sequence of SEQ ID NO: 1 has one or more modifications. For example, the amino acid sequence of SEQ ID NO: 1 has an N-terminal phosphogluconoylation or gluconoylation as disclosed in U.S. Pat. No. 9,567,385, the content of which is hereby incorporated by reference herein in its entirety.

In one embodiment of the present invention, the amino acid sequence of ES135 consists of the amino acid sequence of SEQ ID NO: 1.

As used herein, the term "prevent", "preventing" or "prevention" refers to precluding, averting, obviating, forestalling, stopping, or hindering something from happening, especially by advance action.

As used herein, the term "treat", "treating" or "treatment" refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

As used herein, the term "therapeutically effective amount" or "effective amount" refers to an amount of ES135 to be used in the present invention which prevents, ameliorates or treats the symptoms accompanying a disease or condition referred to in this specification, or provides a desirable therapeutic effect. Therapeutic efficacy and toxicity of ES135 can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

As used herein, the term "administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with a compound, peptide or protein, can include, but is not limited to, providing a therapeutic into or onto the target tissue; providing a therapeutic systemically to a subject by, e.g., intravenous injection whereby the therapeutic reaches the target tissue. "Administering" a composition may be accomplished by oral, injection, topical administration, or by either method in combination with other known techniques.

The term "animal", "subject" or "patient" as used herein includes, but is not limited to, humans and non-human vertebrates such as wild, domestic and farm animals, preferably humans.

III. Embodiments of the Invention

In one aspect, the invention is directed to a pharmaceutical composition for preventing or treating a metabolic disorder in a subject, comprising a protein having an amino acid sequence as set forth in SEQ ID NO: 1.

In another aspect, the invention provides a protein having an amino acid sequence as set forth in SEQ ID NO: 1, for use in the prevention or treatment of a metabolic disorder in a subject.

In still another aspect, the invention provides use of a protein having an amino acid sequence as set forth in SEQ ID NO: 1 in manufacturing a medicament for preventing or treating a metabolic disorder in a subject.

The metabolic disorder includes, but is not limited to, hyperglycemia, impaired fasting glucose, impaired glucose tolerance, insulin resistance, hyperinsulinemia, type I diabetes, type II diabetes, refractory diabetes, and combinations thereof. In some embodiments, the metabolic disorder is insulin resistance. Preferably, the metabolic disorder is type II diabetes.

Hyperglycemia, or high blood sugar, can be defined as a fasting blood glucose level higher than about 7, about 10, about 15, or about 20 mmol/L. Specifically, hyperglycemia is defined as the condition in which a subject has a fasting blood glucose concentration above the normal range, greater than 110 mg/dL (6.11 mmol/L).

Impaired fasting glucose (IFG), is defined as the condition in which a subject has a fasting blood glucose concentration or fasting serum glucose concentration in a range from 100 to 125 mg/dL (i.e. from 5.6 to 6.9 mmol/L), in particular greater than 110 mg/dL and less than 126 mg/dL (7.00 mmol/L). A subject with "normal fasting glucose" has a fasting glucose concentration smaller than 100 mg/dL, i.e. smaller than 5.6 mmol/L.

Impaired glucose tolerance (IGT), which is a pre-diabetic state of hyperglycemia, is defined as a two-hour glucose levels (glycemia) of about 140 to about 199 mg/dL (7.8 to 11.0 mmol) on the 75-g oral glucose tolerance test (according to WHO and ADA). Glycemia of about 200 mg/dL or greater is considered diabetes mellitus.

Insulin resistance is defined as a state in which a normal amount of insulin produces a subnormal biologic response. Insulin resistance can be measured by the hyperinsulinemic euglycemic clamp technique, Homeostatic Model Assessment (HOMA), or Quantitative insulin sensitivity check index (QUICKI).

Hyperinsulinemia is defined as the condition in which a subject with insulin resistance, with or without euglycemia, has fasting or postprandial serum or plasma insulin concentration elevated above that of normal, lean individuals without insulin resistance, having a waist-to-hip ratio <1.0 (for men) or <0.8 (for women). A fasting serum insulin level greater than 25 mU/L or 174 pmol/L is considered hyperinsulinemia. The term "euglycemia" is defined as the condition in which a subject has a fasting blood glucose concentration within the normal range, greater than 70 mg/dL (3.89 mmol/L) and less than 110 mg/dL (6.11 mmol/L).

Type I diabetes results from the body's failure to produce insulin, and has also been called "insulin-dependent diabetes mellitus" (IDDM) or "juvenile diabetes". Type II diabetes results from insulin resistance, a condition in which cells fail to use insulin properly, sometimes combined with an absolute insulin deficiency. It is also called "non insulin-dependent diabetes mellitus" (NIDDM) or "adult-onset diabetes." The defective responsiveness of body tissues to insulin is believed to involve the insulin receptor. Diabetes mellitus is characterized by recurrent or persistent hyperglycemia, and in some examples diagnosed by demonstrating any one of: a. Fasting plasma glucose level≥7.0 mmol/L (126 mg/dL); b. Plasma glucose≥11.1 mmol/L (200 mg/dL) two hours after a 75 g oral glucose load as in a glucose tolerance test; c. Symptoms of hyperglycemia and casual plasma glucose≥11.1 mmol/L (200 mg/dL); d. Glycated hemoglobin (Hb A1C)≥6.5%.

Refractory diabetes is characterized by poor glycaemic control despite adequate treatment. In this condition, even the best therapeutic regimes tailored for rapid symptomatic relief and attainment of glycaemic goals may not work. Many hypotheses, such as poor healthcare-seeking behavior and lack of adherence on part of the patient, clinical inertia, and inappropriate choice of therapeutic regimes on part of the physician, and poor psychosocial support from family members or diabetes care providers have all been suggested as reasons for this state. As illustrated in the literature (J Diabetes. 2016 January; 8(1):76-85), early age of onset, longer duration of diabetes, greater complexity and number of therapies, use of insulin, and presence of microvascular complications are all predictors of refractory diabetes.

In one another aspect, the invention is directed to a method for preventing or treating a metabolic disorder in a subject, comprising administering to the subject a therapeutically effective amount of a protein having an amino acid sequence as set forth in SEQ ID NO: 1. The therapeutic effects of said protein have been proven in the diabetic animal model as described herein.

In some embodiments, ES135 is administered in db/db and ob/ob diabetic animal models for the evaluation of its glucose-lowering effect. Preferably, ES135 is administered subcutaneously (s.c.). In some embodiments, ES135 is administered once, twice, thrice per day or less, e.g., every second day, every third day, every week, every other week, or less. As demonstrated in the present invention, ES135 is administered subcutaneously once. The detailed study procedures are shown in the Examples below.

In some embodiments, administration of ES135 can normalize the level of blood glucose in a subject. In db/db mice, when compared to the vehicle group, ES135 at 0.5 mg/kg SC significantly attenuated the blood glucose level (p<0.05) at $6^{th}$ and $30^{th}$ hr after treatment. ES135 at 1 mg/kg SC also showed statistically significant attenuation of blood glucose levels at $6^{th}$ hr, 18th hr, $30^{th}$ hr and $42^{nd}$ hr after treatment. However, the combination group of ES135 at 0.2 mg/kg with heparin at 500 U/kg showed modest glucose-lowering effect in db/db mice during the study period (FIG. 1)

In ob/ob mice, subcutaneous administration of ES135 at 0.5 mg/kg once significantly attenuated the blood glucose level (p<0.05) at $6^{th}$ hr after treatment compared to the vehicle group. ES135 at 1 mg/kg SC also showed statistically significant attenuation of blood glucose levels at $6^{th}$ hr, $18^{th}$ hr and $30^{th}$ hr after treatment, when compared to the vehicle group. However, the combination group of ES135 at 0.2 mg/kg with heparin at 500 U/kg showed modest glucose-lowering effect in ob/ob mice during the study period (FIG. 2).

Figure 2:
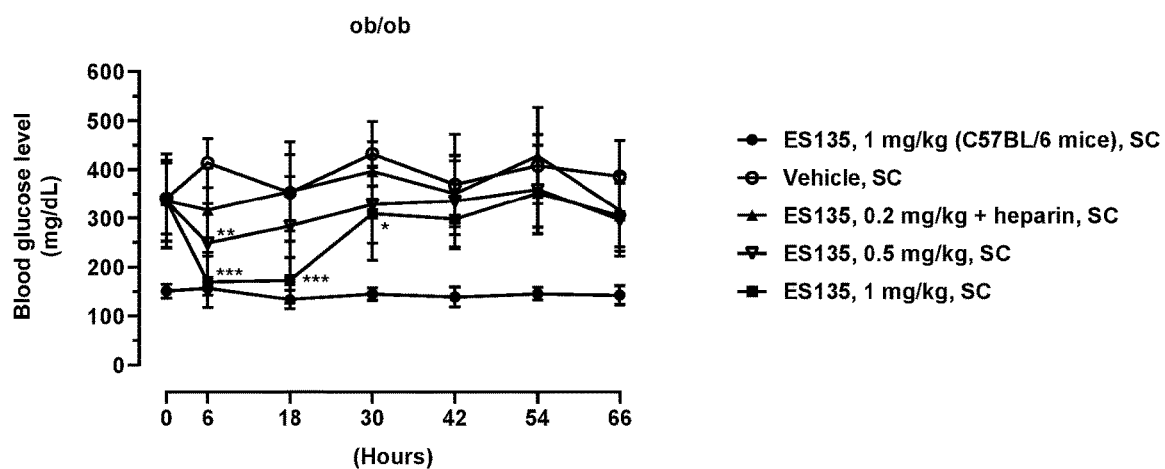
FIG. 2 shows the glucose-lowering effect of different dosages of ES135 in C57BL/6 and ob/ob mice

In C57BL/6 mice, subcutaneous administration of ES135 at 1 mg/kg once did not affect the blood glucose levels during the study period (FIGS. 1 and 2).

In some embodiments, the dose of ES135 administered is equivalent to 0.001-1 mg ES135 per kg body weight (i.e., 0.001-1 mg/kg) of the subject, e.g., equivalent to 0.001-0.01, 0.01-0.05, 0.05-0.1, 0.1-0.2, 0.1-0.4, 0.05, 0.1, 0.2, 0.3, 0.4, 0.5 or higher mg ES135 per kg body weight. As indicated in FIGS. 1 and 2, the glucose-lowering effect of ES135 in diabetic animal models is in a dose-dependent matter. Dose-dependent glucose-lowering effect in both db/db and ob/ob animal models was observed.

In conclusion, treatments of ES135 significantly attenuated the evaluated level of blood glucose.

According to the invention, ES135 may be constituted into any form suitable for the mode of administration selected. Preferably, ES135 is administered subcutaneously, topically, intraneurally, intravenously, intramuscularly, intracerebroventricularly, or intrathecally. More preferably, ES135 is administered subcutaneously.

EXAMPLES

The present invention is more specifically explained by the following examples. However, it should be noted that the present invention is not limited to these examples in any manner.

Glucose-lowering effect after administration of ES135 in db/db and ob/ob mice

ES135 was administered subcutaneously (0.2, 0.5 and 1 mg/kg) once to groups of 8 normal C57BL/6 mice, non-insulin dependent diabetic mellitus (NIDDM) male mice (ob/ob, B6.Cg-Lep<ob>/J and db/db, C57BLKS/J Iar-+Lep-rdb/+Leprdb). All animals were allowed free access to normal laboratory chow and water. Except normal C57BL/6 mice, ob/ob and db/db mice were used when average blood glucose levels were ≥300 mg/dL 3-5 days before administration.

Blood glucose values were measured by tail bleeding from non-fasted animals using glucometer (Optium™ Xceed™ Diabetes Monitoring System, Abbott) at 0 hr (before administration), $6^{th}$ hr, $18^{th}$ hr, $30^{th}$ hr, $42^{nd}$ hr, $54^{th}$ hr and $66^{th}$ hr after ES135 treatment. Serum glucose and the percentage of post-treatment relative to pre-treatment group values obtained was calculated and two-way ANOVA followed by Bonferroni test was then applied for comparison between treated and vehicle groups. Differences was considered significant at *P<0.05, P<0.01 and *P<0.001 vs vehicle control.

While the foregoing written description of the invention enables one of ordinary skill in the art to make and use what is considered presently to be the best mode thereof, those of ordinary skill in the art will understand and appreciate the existence of variations, combinations, and equivalents of the specific embodiments, methods, and examples herein. The invention should therefore not be limited by the above described embodiments, methods, and examples, but by all embodiments and methods within the scope and spirit of the invention.

What is claimed is:

1. A method for attenuating a level of blood glucose, comprising:
    administering to a subject in need thereof a therapeutically effective amount of a protein consisting of the sequence of SEQ ID NO: 1.

2. The method according to claim 1, wherein the protein is administered subcutaneously, topically, intraneurally, intraperitoneally, intravenously, intramuscularly, intracerebroventricularly or intrathecally.

3. The method according to claim 2, wherein the protein is administered subcutaneously.

4. The method according to claim 1, wherein the method is for treating at least one selected from the group consisting of and type II diabetes.

5. The method according to claim 1, wherein the protein is administered at a dose of 0.01 to 1 mg/kg once or twice a day.

* * * * *

SEQUENCE LISTING

```
<160> NUMBER OF SEQ ID NOS: 1

<210> SEQ ID NO 1
<211> LENGTH: 135
<212> TYPE: PRT
<213> ORGANISM: Artificial Sequence
<220> FEATURE:
<223> OTHER INFORMATION: Peptide Modified form Homo sapiens Acid
      Fibroblast Growth Factor

<400> SEQUENCE: 1
```

```
Ala Asn Tyr Lys Lys Pro Lys Leu Leu Tyr Cys Ser Asn Gly Gly His
1               5                   10                  15
Phe Leu Arg Ile Leu Pro Asp Gly Thr Val Asp Gly Thr Arg Asp Arg
            20                  25                  30
Ser Asp Gln His Ile Gln Leu Gln Leu Ser Ala Glu Ser Val Gly Glu
        35                  40                  45
Val Tyr Ile Lys Ser Thr Glu Thr Gly Gln Tyr Leu Ala Met Asp Thr
    50                  55                  60
Asp Gly Leu Leu Tyr Gly Ser Gln Thr Pro Asn Glu Glu Cys Leu Phe
65              70                  75                      80
Leu Glu Arg Leu Glu Glu Asn His Tyr Asn Thr Tyr Ile Ser Lys Lys
            85                  90                  95
His Ala Glu Lys Asn Trp Phe Val Gly Leu Lys Lys Asn Gly Ser Cys
            100                 105                 110
Lys Arg Gly Pro Arg Thr His Tyr Gly Gln Lys Ala Ile Leu Phe Leu
            115                 120                 125
Pro Leu Pro Val Ser Ser Asp
130                 135
```